United States Patent [19]

Jacob

[11] Patent Number: 4,722,936
[45] Date of Patent: Feb. 2, 1988

[54] DEODORIZATION VAGINAL PRODUCTS AND CATAMENIALS

[76] Inventor: Joseph Jacob, 100 Miller Lake Rd., Wooster, Ohio 44691

[21] Appl. No.: 877,147

[22] Filed: Jun. 23, 1986

Related U.S. Application Data

[63] Continuation-in-part of Ser. No. 819,293, Jan. 16, 1986, which is a continuation-in-part of Ser. No. 626,304, Jun. 29, 1984, Pat. No. 4,585,792, which is a continuation-in-part of Ser. No. 492,022, May 5, 1983, abandoned.

[51] Int. Cl.$^4$ .............. A61K 31/34; A61K 31/19; A61K 9/70; A61F 13/20
[52] U.S. Cl. .................. 514/474; 514/557; 514/841; 514/843; 514/921; 514/967; 514/968; 514/969; 424/430; 424/431
[58] Field of Search ............. 424/19, 27, 28, DIG. 14, 424/430, 431; 514/474, 557, 841, 843, 921, 967, 968, 969; 604/891

[56] References Cited

U.S. PATENT DOCUMENTS

| | | |
|---|---|---|
| 2,330,846 | 10/1943 | Sander ................................ 514/560 |
| 2,541,103 | 2/1951 | Sander ................................ 514/560 |
| 2,918,404 | 12/1959 | Mende et al. ....................... 514/772 |
| 3,975,350 | 8/1976 | Hudgin et al. ......................... 424/78 |
| 4,076,663 | 2/1978 | Masuda et al. ...................... 128/285 |
| 4,077,407 | 3/1978 | Theeuwes et al. .................... 424/19 |
| 4,160,020 | 7/1979 | Ayer et al. ............................ 424/15 |
| 4,160,452 | 7/1979 | Theeuwes ............................. 424/19 |
| 4,286,082 | 8/1981 | Tsubakimoto et al. ............. 526/240 |
| 4,374,121 | 2/1983 | Cioca .................................. 514/773 |
| 4,414,212 | 11/1983 | Naylor ................................ 514/223 |
| 4,427,684 | 1/1984 | Ores ................................... 514/328 |
| 4,439,441 | 3/1984 | Hallesy et al. ....................... 514/399 |
| 4,447,562 | 5/1984 | Ivani .................................... 424/81 |
| 4,585,792 | 4/1986 | Jacob et al. ......................... 514/474 |

Primary Examiner—Albert T. Meyers
Assistant Examiner—F. Krosnick
Attorney, Agent, or Firm—Frijouf, Rust & Pyle

[57] ABSTRACT

A method of prophylactics with respect to deodorization by ascorbic acid, salts and esters, topically applied by means of carriers which are otherwise regularly employed in the vaginal area, such as a pharmacological appliance including gauze pads, an absorbant mass or pad associated with menses, douches, and contraceptive compositions.

3 Claims, No Drawings

DEODORIZATION VAGINAL PRODUCTS AND CATAMENIALS

CROSS-REFERENCE TO RELATED APPLICATIONS

This application is a continuation-in-part of application Ser. No. 819,293, filed Jan. 16, 1986, which in turn is a continuation-in-part of application Ser. No. 626,304, filed June 29, 1984, U.S. Pat. No. 4,585,792 which in turn is a continuation-in-part of Ser. No. 492,022, filed May 5, 1983, now abandoned, the specification and claims of the three applications being referred to and incorporated herein by reference.

GENERAL DISCLOSURE

Certain bacteria when present in the human vagina produce virulent poisons called toxins. These toxins, if given entry to the blood stream, are the causative agents of Toxic Shock Syndrome (TSS). TSS is not caused by the invasion of the intact organization into the bloodstream, but by the toxin alone. One means of entry for these toxins is through ulcerations and lesions in the vaginal mucosa, although entry is not limited to mucosal disruption. One common cause of ulcerations and lesions is the use of tampons for catamenial control.

This disclosure explains the discovery that the toxins are inactivated by ascorbic acid. The ascorbic acid is topically applied. Preferably a carrier is used for convenience, such as products intended for use in contact with the or within the vagina and as bandage covering for wounds, such as boils and abrasions. These include pads, sponges, tampons, panty liners and spermicidal gels, among others and gauze dressing for wounds. The addition of ascorbic acid to any or all of these products is useful in improving the health of the user by reducing the risk of TSS.

It is now been discovered, as a result of testing to establish the above discovery, that the menstrual discharge has been very affectively deodorized and that Vitamin C levels in the blood of the user have materially increased by absorption thru the vaginal walls.

The vaginal mucosa is quite absorbant, and it is known that various substances, including drugs, can be introduced into the systemic circulation via this route. It is thus exceedingly important that any perfume or deodorization agent be well characterized and understood not to cause an allergic response or be harmful to the system in any way.

Many women feel more confident and comfortable when using a tampon or pad which has been treated with a deodorant. The treatment used to deodorize tampons at present is by means of fragrances, which do not deodorize in the scientific sense, but primarily mask the odor.

One of the natural characteristics of ascorbic acid is its deodorizing capability. This unique capability comes not by masking odors or dulling olfactory sense in order to reduce ones sense of smell, but by actual reducing odor.

Accordingly, a triple advantage has been discovered for a new use of Vitamin C ascorbic acid in the prevention of toxins which are responsible for toxic shock syndrome, deodorization which is able to give far more confident and comfortable security than mere fragrances, and finally a means of simulataneously supplying an efficient source of Vitamin C to the blood stream.

BACKGROUND OF THE INVENTION

1. Field of the invention

This invention describes the innovative use of ascorbic acid as topically applied to any body where S-aureus may colonize and where access to the bloodstream is available, such as to the vaginal area during menses. The ascorbic acid counteracts the toxins known to contribute to Toxic Shock Syndrome.

Whether or not harmful toxins are produced and neutralized by the Vitamin C, it is a known fact that blood products degenerate during menses, and often produce an undesirable odor.

2. Description of the Prior Art

Numerous articles have been published in scientific journals as well as the popular press regarding Toxic Shock Syndrome, its symptoms and its etiology (*Surgery,* Oct. 1981, 153:4; *Fortune,* Aug. 10, 1981).

It has been discovered that *Staphylococcus aureus,* a commonly occuring bacterium that causes serious infections in humans, existed in the vaginas of almost all the female victims of Toxic Shock Syndrome. However, it is noted that *Staphylococcus aureas* does not initiate Toxic Shock Syndrome as a result of the invasion of the intact organism into the blood stream. Instead, *Staphylococcus aureus* colonizes in the vaginal cavity which technically is located outside the body. As *Staphylococcus aureus* grows and multiplies, it produces at least two virulent poisons which have been identified as Pyrogenic Exotoxin C and Staphylococcal Entertoxin F. These toxins then enter the bloodstream of the victim, by way of micro-ulcerations in the vaginal wall, and by gaining access through the exposed endometrial vascular bed after endometrial sloughing during the initial phase of menstruation.

One means of entry for these toxins has been linked to the use of tampons, since tampons are known to cause ulcerations and lesions in the vaginal mucosa. *Annals of Internal Medicine,* June 1982, Vol. 96, No. 6 (Part 2) p. 855, Column 2. However, the disease is not limited to tampons, or to women. Any place where S-aureus can colonize, and can gain access to the bloodstream, develops a potential danger of developing TSS. Men have been victimized by entry to the bloodstream from a boil.

We have found that only after entering the bloodstream, do the toxins act systemically and elicit the symptoms associated with Toxic Shock Syndrome. These symptoms include high fever, diarrhea, vomiting and rash followed by a rapid drop in blood pressure and vital organ failure resulting in a mortality rate of approximately 6% of those who contract the disease. There is no known prior art teaching to the discovery of the present invention.

A study of odor reduction in food products has been conducted by Japanese inventors, such for example as the work Koho Kakaia disclosed in the Japanese Pat. No. 93,184,635 issued July 28, 1980 for Soybean Milk Deodorant. Japanese Pat. No. 8,547,662 issued Mar. 15, 1985 teaches fish texture and odor modification of meat substitutes by the use of ascorbic acid.

An object of this invention is to detoxify toxins produced by bacteria as opposed to destruction of the bacteria.

Another object is to place detoxification agents in the area where toxin producing bacteria may colonize, to thereby destroy toxins before they can cause deleterious effects.

A still further object is to use the substances normally employed for feminine hygiene and birth control, or coverings for sores and wounds, as carriers for ascorbic acid.

Yet another object of this invention is to simultaneously provide detoxification and deodorization of menstural discharge.

Yet another object of the invention is to provide Vitamin C dosing directly to the systemic circulation via the vaginal mucosa.

SUMMARY OF THE INVENTION

This invention is the discovery that ascorbic acid when topically applied to open wounds or to the vaginal area of a human female during menses will inactivate the toxins known to contribute to Toxic Shock Syndrome.

The toxin which is responsible for Toxic Shock Syndrome is essentially that produced by staphylococcus aureus. There may possibly be other toxins produced by other bacteria.

The novel approach of this invention, is the focus on detoxification of the toxic product of bacteria, rather than an attempt to eliminate the bacteria.

It has been discovered, according to this invention, that ascorbic acid is outstandingly effective in detoxification of the toxins found in the vaginal area of a human female host and on open wounds. Although ascorbic acid is known to be a strong antioxidant, it is not known by the inventor of this approach how the ascorbic acid inactivates the toxin. Toxin structures are as yet unknown and the chemistry of this invention is unknown.

It is known, by the discovery of this invention, that the external administration of an effective amount of ascorbic acid to open wounds or the vagina of a human female host will detoxify any toxins to the point of substantially eliminating the danger of Toxic Shock Syndrome.

The discovery of this invention is based on the fact that bacterial *S-aureus* do not invade the blood system of the host to cause TSS, and if they do invade the blood system it is not the bacteria that causes TSS, but rather that *S-aureus* produces a toxin so potent that a very small amount in the blood system of a host will produce horrendous symptoms of Toxic Shock Syndrome, including death.

The invention, then, is the astonishing discovery that ascorbic acid or its equivalent forms, will fully and completely neutralize and detoxify the real culprit, the toxins known as Pyrogenic Exotoxin C and Staphylococcal Enterotoxin F, and is itself a beneficial substance with no known side effects.

The fortunate discovery of deodorization while making the study of the antitoxin effect, has added a further and highly benefical secondary benefit to the use of ascorbic acid when applied in a pharmacological appliance including gauze pads, an absorbant mass associated with menstruation douches, and contraceptive compestions and devices as carriers. To be certain of effective use, the ascorbic acid its salts or esters on or within the carrier should be in an amount of at least 100 mg for each carrier or dose.

The ascorbic acid is topically applied into the vagina, or around the vulva by any means one may choose. Manual insertion by a pump device, or simply inserting a tablet into the vagina is within the concept of this invention.

However, as a practical fact, the ascorbic acid will be physically entrapped in the interstitial spaces of a tampon, napkin, or pad, and will be mixed with the ingredients of a water based douche. Spermicides and birth control sponges may be used as carriers without interfering in any way with the intended function of such carriers.

There is no practical means of knowing in advance whether the detoxifying ascorbic acid will be needed when applied by these carriers, but ascorbic acid is a compatible substance with any such product, and will neutralize any toxin, if the toxin is produced.

This invention has no quantity limits. As a practical application, however, about 100 mg is a suggested minimum, and 5 g exceeds the predicted necessary upper limit.

*S-aureus* bacteria may be present in very small numbers, and thus produce a very small quantity of toxin. That small amount, if entering the blood system, is all that is needed to produce the dreadful TSS.

There may be a huge colony of *S-aureus*, producing much toxin, but gaining no access to the blood system. Hence, no adverse results arising from *S-aureus* will be noted.

There is no means of predicting the amount of toxin that is present, and therefore no way to predict the precise amount of ascorbic acid needed. Such tailoring of the dosage for general consumption would be totally impractical in any event.

Therefore, from supportive studies and experiments to establish this invention, it has been determined that 100 mg as a lower limit for an adult human female host will be a safe lower limit. Because caution dictates being over-cautious, it is recommended that up to 500 mg per application be used. Ascorbic acid has not exhibited any adverse side effects in this large amount.

In testing the deodarant capability of ascorbic acid, it has been found that the lower limit of 100 mg is recommended, in order to assure a complete and satisfactory deodorization. A lower amount might be effective in most instances, but the 100 mg level is a preferred lower limit to be certain that all cases are adequately protected. There is no upper limit, but 500 mg is more than sufficient for the most cautious user.

DEFINITIONS

Toxin: (Bacterial) Toxin produced by bacteria. Includes exotoxins, which diffuse from bacterial cells into surrounding medium, and endotoxins, which are liberated only when the bacteria cell is destroyed.

Detoxify: To remove the toxic quality of a substance. (detoxification: detoxicate).

Detoxifying Amount: Any amount will detoxify some toxin, but about 100 mg minimum is operative to provide safe detoxification.

Topical Carrier: Topical: Greek (topos) place. Pertinent to a definite area; local. (Tabers Encyclopedic medical Dictionary. F. A. David Company, Phila. Pa)

Carrier: . . . that which carries: . . . a . . . , support, . . . on which something is carried . . . Webster's New Twentieth Century Dictionary. Second Edition.

Ascorbic acid shall be used generically to include the acid form, salts, esters or derivative thereof known for their therapeutic usefulness in the human system.

DESCRIPTION OF THE PREFERRED EMBODIMENT

Ascorbic acid has important properties in that the dry crystals are stable in the air for a very long period of time. However, once ascorbic acid enters into solution, it is capable of undergoing oxidation in a variety of reactions. The tendency of ascorbic acid to be oxidized increases with increasing pH. ("The Antioxidant Vitamins", CRC Critical Review, *Food Sciences & Nutrition*, March 1979, pp. 271).

Ascorbic acid is added, according to this invention, to the appropriate carrier at milligram levels, which is completely compatible with the pH of the vaginal cavity.

Although it has not been determined how ascorbic acid functions to detoxify bacterial toxins, it is known that ascorbic acid possesses relatively strong reducing power as is shown in its ability to decolorize many dyes. (Merck Index, 8th ed.). These kinds of reactions may be accelerated by alkalies, iron ions and copper ions. In order to achieve the same chemical effect as ascorbic acid, very strong chemical reducing agents would be required.

Also, ascorbic acid is capable of reducing the disulfide bonds in proteins and toxins to free sulphydral groups, thus resulting in their biological inactivation (Charles E. Clark and T. J. Smith, "Effects of Ascorbic Acid (AA) on Diphtheria Toxin and Intoxicated HELA Cells," *Journal of Nutritional Science, Vitaminology*, 22 (1976) 313–319).

The above described reducing power is probably the reason that compounds which are manifested as disagreeable odors are changed in character to a form which is non-offensive.

Ascorbic acid has demonstrated biological activities that are capable of completely inactivating Diphtheria exotoxin in vitro (ibid) at concentrations of 90 micrograms ascorbic acid per milliliter. In order to achieve the same effect, strong reducing agents such as para-methylaminophenyl sulfate or 2-mercaptoethanol would be required. However, compounds such as these would cause deleterious effects on biological tissues if administered to humans.

There appears to be no known approach to TSS prevention using ascorbic acid. This new use of a very safe product has been discovered, according to this invention, to posses essentially fully and complete prophylactic power for prevention of TSS.

We do not know the mechanism by which ascorbic acid renders the staphylococcal toxins ineffective, but we are aware that ascorbic acid will act as a reducing agent, an antioxidant and a free radical sequestering agent. We also, from in vitro testing, know that it does inactivate the causative agents in Toxic Shock Syndrome.

Ascorbic acid is known to oxidize to dehydroascorbate. By a series of intermediate reaction steps, a protein or toxin, may interact with the ascorbic acid and any intermediates to break the disulphide bond and produce reduced sulfhydral group. It is necessary to emphasize that this invention is a result of discovery and that the actual mechanism of detoxification is not yet known.

In addition to the staphylococcal toxins, menstrual blood contains a variety of proteins which are broken down to malodorous and toxic substances. It is also possible that ascorbic acid plays an important role in inactivating these endogenous toxic proteins before they are absorbed into the body.

In the foregoing disclosure there has been no reference to catalytic agents and in fact catalytic agents are believed to be unnecessary in most instances. There are sufficient metallic ions present in most environmental situations to serve any catalytic requirements of the oxidation of ascorbic acid. Nevertheless, in order to assure completion of the test results, and in actual commercial use it is recommended that some additional cupric$^{++}$ ion be provided in order to assure a complete reactions sequence.

Again, there are many possible and unknown reactions of ascorbic acid and toxins, but from a careful review of the observed action according to this invention, and from extensive theoretical studies, the above effect is probably at least one of the major reactions taking place in this invention. In this reaction sequence, ascorbic acid is the reductant, and the cupric$^{++}$ ion is the pro-oxidant which initiates the reaction. The cupric$^{++}$ ion is reduced to the cuprous$^{+}$ ion (Cu$^{+}$), along with molecular oxygen. For each molecule of ascorbic acid that is oxidized to dehydroascorbate, a molecule of hydrogen peroxide is liberated. Hydrogen peroxide is a powerful oxidant when in the presence of cuprous$^{+}$ ion and is capable of generating hydroxyl radicals according to the reaction below:

$$Cu^+ \text{-} 1e^- + H_2O_2 \text{-----} Cu^{++} + .OH + HO^-$$

On the product side of the equation, the hydroxyl free radical (.OH) that is formed is very reactive and is known to participate in reactions that irreversible inactivates proteins.

It is recognized, however, that this invention is based upon laboratory observation of the inactivation of a toxin and the substantiation of such by laboratory animals. Accordingly, the above theory is supplied as the best explanation that reasonable minds conceive, but the invention herein disclosed is based upon actual testing and not on the above theory. There are a number of inter-related reaction sequencces, in addititon to the ones described above, that could contribute to the toxin inactivation.

As a means for supporting the presentation made herein, a supply of Enterotoxin F was obtained from Dr. Bergdoll at the University of Wisconsin. Eighteen rabbits were injected intravenously with 10 micrograms per kilogram of body weight of Staphylococcal Enterotoxin F. Nine of the rabbits developed severe diarrheal illness and died within 72 hours. Three additional rabbits developed severe diarrhal illness but survived. Six rabbits developed no grossly detectable signs of illness. The ten micrograms per kilogram dose therefore appears to be close to the LD 50 (Lethal Dose in half) for this group of rabbits.

Fifteen rabbits were then injected with 10 micograms per kilogram of the same toxin which had been preincubated for one hour at room temperature with 1.0 milligram of ascorbic acid. None of the fifteen animals so challenged showed any signs of illness whatsover.

On the basis of these data, ascorbic acid has demonstrated a statistically significant effect in neutralizing the Staphylococcal Enterotoxin F.

It must be emphasized that testing of this invention on a human host can never be completely conclusive for the simple reason that there is no means of predicting which person may develop TSS. However, it has been completely established that it is the toxin entering the blood stream that causes the Toxic Shock Syndrome. It is submitted that by injecting the toxin into test animals results in a complete and conclusive means for establishing the toxicity effect upon the living animal. Therefore, the destruction of the toxin's ability to affect the animal is likewise fully and conclusively established.

Therefore, this invention is a prophylactic that can be safely used in substantially unlimited concentration because of its known compatibility with the human system, even in massive doses, and accordingly, having been established in its ability to inactivate the causative toxins of TSS, it is safe to use on the general public as a prophylactic for the delerious toxins that are often produced by staphylococcal bacteria.

PROTOCOL

To a solution of ascorbic acid prepared at a concentration of 1.0 milligram per milliliter in a 120mM phosphate buffer pH 7.4 containing 1 mM cupric chloride, add the appropriate amount of toxin, based on a dose of 10 micrograms of toxin per kilogram of body weight, to a 1.0 ml volume solution of ascorbic acid, so that it can be easily injected. For example, 30 micrograms of toxin per milliliter of ascorbic acid solution to be administered to a 3 kilogram rabbit. This step can be accomplished using any of the soluble forms of ascorbic acid, such as the free-acid or the sodium salt. Care should be taken to keep the pH at about the 7.4 range to be compatible with intravenous injection. In addition, the solution of ascorbic acid should be protected from light. The crystalline form of ascorbic acid when used in commercial distribution, will not be effected by light, but in this protocol the solution should be protected from light, The toxin and the combination of toxin with ascorbate should be kept at room temperature for 1 hour to simulate time in the vagina prior to toxin absorption. At the end of that time, the entire material injection intravenously into the rabbit.

This procedure will allow the interaction(s) to occur between toxin molecule and the ascorbate molecule. The injection into the animal is of the entire 10 micrograms per kilogram dose of the toxin.

In order to place the ascorbic acid into position to serve as an effective prophylactic, it must be placed in the area where lesions may form at the time the toxins are known to form. Accordingly, it is desirable to place the crystalline form of the ascorbate on a carrier device that may reside in the vagina during menses, as a napkin over the vulva, in birth control sponges, panty liners, spermicidal gels, and douche, among others.

The popular available tampon is an ideal carrier which requires no new technology to construct. It has been found that the interstices of the tampon, whether the woven or molded non-woven fabric, is controllable to entrap the crystals of the ascorbic acid in a quantity ranging from 100 to 5,000 milligrams, and that lower quantity limit has been found to be sufficient for the intended purpose.

The method of using the tampon as a prophylactic for the Staphylococcal toxin is to simply provide the commericially available tampon as an insertable carrier for the vaginal of a human host. The ascorbic acid is added to the assorbent material either by surface dusting or placing a quantity of material within the body of the absorbent material, and inserting the tampon carrier into the vagina during menses. Also, a solution of ascorbic acid may be used to soak the carrier, and when dry the crystalline material remains. The dry method is perfect for tampon, napkins, liners, and similar fibrous wear.

It is necessary that the ascorbic acid be available to the cervix and vaginal mucosa of a human host in an effective amount, whether on the surface or within the body of the tampon.

For those who do not wish to use a tampon, or possibly during light periods of menstrual fluid production near the end of the cycle, it has been found to be effective to incorporate the ascorbic acid with a carrier which does not have an ingredient that will deleteriously react with the acid.

As an example, a base of inert aqueous pharmaceutical material as set forth below serves as a suitable carrier.

glycerin 5-10% (w/w)
sodium carboxymethylcellulose 10-20% (w/w)
sodium alginate 5-15% (w/w)
polyethylene glycol 5-12% (w/w)
boric acid 1% (w/w)
ascorbic acid 0.1-2% (w/w)
water to 100%

Therefore this invention is prophylactic that can be safely used in substantially unlimited concentration because of its known compatibility with the human system, even in massive doses, and accordingly, having been established in its ability to inactivate the causative toxins of TSS, it is safe to use on the general public as a prophylactic for he deleterious toxins that are often produced by staphylococcal bacteria.

The problem remains, then, of how to place ascorbic acid where it is needed without introducing side effects or destroying the effective properties thereof. Although manual topical application is within the penumbra of this invention, such application is not very practical.

This invention therefore, embraces the concept of combining ascorbic acid with the carriers which are products available in commercial usage. Examples of such products are in three categories:

(1) those associated with menses
(2) those associated with birth control, and
(3) those associated with cleaning the vagina.

Another category of use which is of great value is the intravenous ascorbic acid therapy for toxin syndromes.

TSS is usually associated with women, during menses. Statistical studies lead to the conclusion and the greatest number of female victims were those who had used super absorbant tampons during menses. The cause is considered to be the drying of the vaginal mucosa, resulting in lesions. *S-aureus,* which is always present in the vagina, produces the toxins pyrogenic exotoxin-C and enterotoxin-F. If the disruptives of the vaginal mucosa are open when the toxins are present, they enter the blood stream and TSS results.

FIRST CATEGORY CARRIERS

"Sanitary napkin" is a term used for a pad of absorbent material held in place over the vulva by belts or straps to catch the menstrual discharge. With the advent of insertable tampons, the sanitary napkin is often used only during high flow periods.

There is relatively little danger of toxic poisoning when using exterior napkins because of the large flow, but more importantly there is little cause for mucosa disruption.

Nevertheless, toxin is often present and abrasions do occur. To prevent toxin poisoning, such napkins are provided with ascorbic acid physically entrapped in the interstices of the napkin.

The object is to place an abundance of the acid in the area which contacts the flesh. Dusting is the most direct and simple method when using woven fabric, and mixing with bonded non-woven slurry before molding is effective.

To assure safety, it is recommended that at least 100 mg ascorbic acid are available to fluids reaching the surface of the napkin. This level will detoxify toxins in the greatest concentration known to develop. In a commercial napkin, as much as 5,000 mg have been found to produce no deleterious effect.

The ascorbic acid may also be incorporated throughout the entire napkin by dusting the body of material during manufacture, or by wetting with the solution in an inert atmosphere and allowing to dry. Dusting during or after manufacture is the recommended best procedure.

The manufacture and use of an insertable tampon is fully described and claimed in U.S. Pat. No. 4,585,792 as referenced above. Panty liners are actually lighter versions of the sanitary napkin, and ascorbic acid is incorporated in the same manner.

SECOND CATEGORY CARRIERS

Spermicidal Products

Because a lesion may occur at any time, and by many causes, it is beneficial to include the ascorbic acid or derivatives thereof with all products of the four listed categories.

As an example of a spermicidal composition which may carry ascorbic acid, a composition containing a vehicle and spermicide as set forth in U.S. Pat. Nos. 2,330,846 and 2,541,103 with about 100 mg to 500 mg ascorbic acid added, is effective for both spermicidal and detoxification functions.

This invention is in the discovery for the means for safely and effectively eliminating the dangerous toxin of *S-aureus*, and the combination with a contraceptive carrier provides a product having a utility for dispersion and delivery to areas where toxin may be produced.

A general specification for a contraceptive is:

Spermicides

Active ingredients:

By weight:

Spermicidal agents octoxynol 1–5% or nonoxyl 3–15% ascorbic acid 1–5%

Carrier system:

propylene glycol 1–5% stearic acid 1–5%

Polyethylene glycol 2–4%

Starch 1–5%

Water; to make 100%; adjust pH to 4.5–5.0.

Product Form:

Jelly, cream, foam

Specific Forms

The following are various vaginal preparations which are compatible with ascorbic acid added to give anti-Toxic Shock Syndrome Toxin protection.

(1) Contraceptive foam

Typical composition:

nonoxyl-9 5–15% propyleneglycol 2–5% isopropyl alcohol 3–6% polyethlene glycol 2–4% propellent, air, etc.; water, pH adjusted to 4.5 to make 100%

(2) Contraceptive Jellies

Octoxynol 1.0–2.0%

Carrier System; Propylene glycol, water, sorbitol, starch, (Adjusts to pH 7.4)

(3) Contraceptive sponge sponge shaped to fit over cervix sponge contains: nonoxynol 1 gram, ascorbic acid 1 gram Inert ingredients:

Sodium metabisulfite

Citric acid in water adjust to pH 4.5–5.0

The sponge has interstices which are filled by compression and release, under inert gas atmosphere.

THIRD CATEGORY CARRIERS

Douche

Another carrier vehicle to utilize the invention is the douche. The specifications for douche are:

(1) compatible pH (4.0–6.0)

(2) sterile (3) hypotonic-isotonic 4) ascorbic acid 0.1–10.0 mg/ml buffered to pH 4–6 with appropriate buffer (e.e., acetic acid/sodium acetate)

The douche may be prepared and stored under anaerobic conditions (to enhance acid stability) as a solution or as a powder to which water is added prior to use.

Example Formulas are:

Solution (1) 250 ml H20

(2) Sodium acetate buffer o.05 M, (pH 5.0)

(3) ascorbic acid 1.0 mg/ml (4) Mixed 1 hour, under N2 gas phase (5) Check pH, adjust to pH 5 with 0.1 N NaOH or 0.1 N HC1.

(6) Filter through 0.2 micron filter for sterility.

(7) Store in dark glass or plastic container to prevent degradation by light.

(8) Store sealed under N2 to prevent decomposition.

Dry Packet (1) Sodium acetate 210 mg (2) ascorbic acid 100 mg

Directions: Add contents of packet to 250 ml water, mix until powder dissolves, and use within 1 hour.

In order to verify the results of testing using toxin produced by *S-aureus*, an experiment was performed using skin method of John P. Craig. In this method, a bacterial toxin, i.e. cholera toxin from *V cholerae,* was injected intradermally into the shaved skin of rabbits. The toxin at doses of 1 and 5 nanograms was effective in causing vascular leakage in the skin. This toxin effect was completely blocked by mixing the toxin with ascorbic acid (0.01 mg/ml and higher). Other organic acids, such as pyruvic acid and maleic acid were not effective antitoxins at 1 mg. Thus, the antitoxin activity of ascorbic acid is specific and not found with the other organic acids at even 100 times the concentration of the ascorbic acid.

INTRAVENOUS ASCORBIC ACID THERAPY FOR TOXIC SYNDROMES

Although toxic shocl syndrome can be essentially prevented if the disclosure above is followed faithfully, the toxic syndrome nevertheless will occur because of laxity and also from unsuspecting sources such as cuts, abrasions, boils and other skin eruptions. The syndrome is exceedingly distressful and does result in death in a considerably proportion of the numbers of persons who contract the disease.

Having seen the miraculous results of syndrome prevention as disclosed above, it has also now been discovered that those who nevertheless contract the disease, toxic shock syndrome is treatable, according to the further findings of this invention, by the intravenous administration by constant infusion of ascorbic acid. Constant infusion apparatus and methods are well known to the medical arts, and widely employed in administering insulin.

Because human testing is prohibited at this stage of the development of the invention, the efficiency of this means of treatment was shown by treating five rabbits that had been given lethal toxic shock syndrome toxin injections. A 4 hour infusion of ascorbic acid in normal saline (10 mg ascorbic acid kg body weight/hour) was effective in preventing death in any of the rabbits. A complete cure was accomplished.

What is claimed is:

1. The method of preventing malodor due to the blood degradation during menses comprising administering a deodorizing effective amount of ascorbic acid to the cervix or vaginal mucoss.

2. A method of preventing malodor due to the blood degradation during menses comprising administering a deodorizing effective amount of ascorbic acid to the cervix or vaginal mucosa by means of a carrier selected from the group consisting of gauze pads, douches, and contraceptives composition.

3. In the method of claim 2, said ascorbic acid being supplied in a minimum of about 100 mg of ascorbic acid physically entrapped in the interstitial spaces of all but the douches and mixed into the douches.

* * * * *